United States Patent [19]
Baudonniere et al.

[11] Patent Number: 5,983,128
[45] Date of Patent: *Nov. 9, 1999

[54] DEVICE FOR EXAMINING A SUBJECT AND, IN PARTICULAR, DETERMINING HIS OR HER VESTIBULAR EVOKED POTENTIALS

[75] Inventors: Pierre-Marie Baudonniere, Pas; François Jouen, Paris; Jean-Claude Lepecq, Nancy; Bernard Renault, Paris, all of France

[73] Assignee: Centre National de la Recherche Scientifique, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/765,958
[22] PCT Filed: Jul. 11, 1995
[86] PCT No.: PCT/FR95/00931
  § 371 Date: Jan. 10, 1997
  § 102(e) Date: Jan. 10, 1997
[87] PCT Pub. No.: WO96/02186
  PCT Pub. Date: Feb. 1, 1996

[30] Foreign Application Priority Data

Jul. 15, 1994 [FR] France .................................. 94 08816

[51] Int. Cl.$^6$ ....................................................... A61B 5/10
[52] U.S. Cl. ........................................... 600/544; 600/595
[58] Field of Search ................................... 600/544, 545, 600/546, 554, 595, 558, 559

[56] References Cited

U.S. PATENT DOCUMENTS

| | | | |
|---|---|---|---|
| 4,305,402 | 12/1981 | Katims | 600/545 |
| 4,503,863 | 3/1985 | Katims | 600/545 |
| 4,672,978 | 6/1987 | Danto | 600/544 |
| 5,143,081 | 9/1992 | Young et al. | 600/554 |

FOREIGN PATENT DOCUMENTS

WO 83/03341  10/1983  WIPO .

OTHER PUBLICATIONS

PCT Search Report for PCT/FR95/00931, Oct. 2, 1995 (French and English versions).

Acta Otolaryngol, vol. 102, 1986 Stockh., SE, pp. 175–178; Richard Kast, et al., "Otolithic Evoked Potentials: A New Technique for Vestibular Studies".

Electroencephalography and Clinical Neurophysiology, vol. 80, No. 2, Mar. 1991 Ireland, pp. 140–145; J. Elidan et al. "Short and Middle Latency Vestibular Evoked Responses to Acceleration in Man".

Medical Progress Through Technology, vol. 20, No. 1–2, Jan. 1994; Amsterdam, NL, pp. 31–35; Caupolican Munoz–Gamboa et al., "Human Vestibular Evoked Responses".

*Primary Examiner*—Robert L. Nasser

[57] ABSTRACT

A frame (1) with driving members (9–11) for translating and/or rotating an assembly (4) movably mounted in said frame along one of the three planes defining the space. A unit for mechanically controlling said driving members is arranged to enable the stationary patient on the movable assembly (4) to be exposed to a moving elementary stimulation having monotonic space-time characteristics with a speed- and/or acceleration-adjustable profile, by translation and/or rotation thereof along at least one of said three planes of the space. The device further includes a processing unit for digitising waves sensed by at least some of the electrodes of an electrophysiological helmet on the patient's skull, and for finding therein evoked potentials that match the profile of the elementary stimulation. Real-time data on the functioning of at least one part of the vestibular system may thus be obtained.

13 Claims, 5 Drawing Sheets

DEVICE FOR EXAMINING A SUBJECT AND, IN PARTICULAR, DETERMINING HIS OR HER VESTIBULAR EVOKED POTENTIALS

The invention concerns a device for examining a subject and, in particular, determining his or her vestibular evoked potentials by stimulation of his or her vestibular system.

By subject there is to be understood any living being provided in particular with a vestibular system, whether the subject is clinically ill, in which case it is a question of a patient, or whether the subject is clinically healthy.

The vestibular system can be considered diagrammatically as a system of accelerometers allowing the central nervous system of a subject to measure the resultant both of gravity and of the accelerations in the three planes defining space.

The vestibular system consists of two functional sub-systems which are distinct but complementary. The first sub-system, termed canal sub-system, comprises the so-called semi-circular canals, which are clearly assigned to the measurement of the angular accelerations of the body. The second sub-system, termed otolithic sub-system, is divided into two parts which provide two complementary functions: the utricular system and the saccular system. The first function provided concerns the analysis of the variations of the gravitational forces linked to gravity, and the second function is measurement of the linear accelerations in the three planes which define space (plane X (sagittal), plane Y (lateral), and plane Z (vertical)), as demonstrated by HIXSON, W. C.,; NIVERI, J. J.; CORRELA, M. J., in their article "Kinematics nomenclature for physiological accelerations with special reference to vestibular applications", Monograph 14, Naval Aerospace Medical Institute, Naval Aerospace Medical Center, Pensacola, Fla., 1966.

Since the vestibular system is to a great extent responsible for the balance of a living being, and in particular of a human, it is necessary to be able to test its functioning specifically, either to verify its integrity or to detect the various pathologies thereof and/or to measure the effects of the vestibular therapies.

Such a test can be carried out by specifically stimulating the vestibular system.

In fact, stimulation of the vestibular system, like that of numerous other parts of the nervous system, generates brain activity waves originating from identifiable regions of the brain, which waves, called evoked potentials, can be picked up in particular at the level of the scalp of an individual.

There are thus visual, auditory or somesthesic evoked potentials, which are used every day in neurology, since their origin is relatively well known. In contrast, very little is known of the origin of the vestibular evoked potentials (VEPs).

The principal reason for this lack of knowledge of the cerebral zones generating VEPs lies in the anatomophysiology of the vestibular system which is controlled by the central nervous system in its sub-cortical part. The so-called "second order" vestibular neurones are already centres of processing and integration of the stimulation issuing from the peripheral vestibular system. These second order neurones are termed polyafferent, since they are linked to a large number of nervous structures, which are involved in the unconscious regulation of the posture. Consequently, it is difficult to determine precisely which are the cortical projection zones of the vestibular system.

Up to now, research carried out on the vestibular system has essentially concerned the vestibular evoked potentials linked to the stimulation of the first subsystem comprising the semicircular canals. This research has been made possible by the perfecting of devices making it possible to rotate the body of a subject. Certain vestibular projection zones involved in the sensations of rotation have thus been able to be shown up by means of such devices.

Although the evoked potentials of canal origin are relatively well documented, in contrast the evoked potentials of otolithic origin (second vestibular sub-system), induced by linear acceleration, are virtually unknown. Up to now, only one experiment has given results. This was carried out by KAST and LANKFORD. It is described and analysed in the article: KAST, R. and LANKFORD, J. E., "Otolithic evoked potentials: a new technique for vestibular studies", 1986, Acta Otolaryngol., 102, 175–178.

The KAST and LANKFORD device comprises:

a frame housing an assembly which is movable in at least one direction within the said frame and capable of supporting and immobilising a subject, drive means capable of moving the said assembly in at least one direction in order to stimulate the vestibular system of the subject, an electrophysiological helmet which can be fitted onto the scalp of the said subject and is provided with a plurality of electrodes, in selected respective positions, each electrode being capable of detecting brain activity waves issuing from identifiable regions of the brain, means for mechanically controlling the said drive means according to a selected law of motion, and also processing means capable of picking up the waves detected by the said electrodes in order to obtain evoked potentials therefrom, and to seek such evoked potentials which match the selected law of motion.

In such a device, the living being, a human, is stretched out on a slightly inclined table. The vestibular stimulation, in particular otolithic stimulation, is obtained by dropping the head along a vertical axis with respect to the ground. The electrophysiological helmet comprises four electrodes. Moreover, the subjects examined are all normal (without attested neurological or vestibular pathology).

A device of this type has a certain number of drawbacks.

A first drawback lies in the fact that the otolithic stimulation is not strictly linear, since the subject is stretched out on an inclined plane, which means that the stimulation used combines both translation and rotation at the same time.

A second drawback lies in the fact that the results were obtained on normal subjects, which means that the said results were not the subject of any validation by the examination of subjects suffering from an otolithic disorder.

A third drawback lies in the fact that the electroencephalographic cover offered by the electrophysiological helmet is particularly poor and does not permit precise topographical analysis of the parts of the brain involved in the vestibular response.

A fourth drawback lies in the fact that the visual, auditory and somesthesic afferences were not particularly well controlled and could therefore parasitise the vestibular evoked potentials studied.

Afferences are understood to be the information conveyed by peripheral neurone paths in the direction of the central nervous system. This information, issuing from different parts of the body, is superposed on the information issuing from the vestibular system of the subject. Thus, the installation of a subject in an unsuitable chair, in which he or she does not feel at ease, constitutes a parasitic somesthesic afference.

A fifth, and not the least, drawback lies in the fact that, on the one hand the duration of the stimulations is not short enough, which means that they cannot be regarded as punctual and, on the other hand, the stimulation profile is substantially sinusoidal, since the subject is subjected to variable accelerations followed by variable decelerations, without any intermediate period of rest. Under such conditions, it is particularly difficult to isolate a specific response of the otolithic system.

Finally, a last drawback lies in the fact that the device perfected by KAST and LANKFORD made it possible to expose the subject to one, and only one, type of stimulation profile (sinusoidal).

The object of the present invention is to improve the situation, by providing solutions to these problems.

A first object of the invention is to permit either a specific study of the first sub-system, termed canal sub-system, or of the second sub-system, termed otolithic subsystem, or a coupled study of these two sub-systems.

A second object of the invention is to propose numerous different stimulation profiles which can be adapted to the pathology of the subject to be examined.

A third object of the invention is to improve substantially the sensitivity of detection of the cerebral zones involved in the vestibular projection.

A fourth object of the invention is to be able to be more certain of the vestibular origin of the stimulation, by controlling the parasitic auditory, visual and somesthesic afferences of the subject.

A fifth object of the invention is to propose a device comprising processing means capable of analysing and processing the vestibular evoked potentials in real time.

Finally, a sixth object of the invention is to make available, in the same device, and in automated form, a group of predefined examinations, and also a data base comprising test examinations permitting comparisons with one or more examinations carried out previously.

To this end, the invention proposes a device for testing a subject, of the type defined previously, and wherein the drive means are arranged so as to permit displacement of the said assembly in translation in at least one of the three directions defining space, and/or displacement of the said assembly in rotation in one of the planes defining said space, wherein the means for mechanically controlling the said drive means are arranged so as to permit the application to the subject of a moving elementary stimulation having monotonic space/time characteristics, with a profile which is adjustable in speed and/or acceleration, in at least one of the said three directions of space in translation and/or in at least one of the said three planes of space in rotation, and wherein the processing means are capable of digitising the waves detected by some, at least two, of the said electrodes, and are arranged to seek therein evoked potentials which match the profile of the elementary stimulation.

This makes it possible to obtain information in real time regarding the functioning of at least a part of the vestibular system and, more specifically, either of the canal sub-system or of the otolithic sub-system, or of a combination of these two sub-systems.

According to another characteristic of the invention, the processing means are additionally capable of storing space/time examination characteristics, each examination being defined by the repetition of at least one stimulation cycle of at least one elementary stimulation phase selected from a first phase in which the assembly is subjected to acceleration in a given direction or a given direction of displacement, a second phase in which the assembly is subjected to a constant translation or rotation speed in that same direction or that same direction of displacement, and a third phase in which the assembly is subjected to deceleration in a direction or a direction of displacement opposed to that of the first and second phases.

Thus, the invention makes it possible to subject a living being to accelerations or decelerations of the linear and/or rotatory type on command. But it also makes it possible, during constant speed phases, to provide periods of non-stimulation during which the vestibular system of the living being is not stressed.

In an embodiment of the invention, the acceleration of the first phase is of an intensity of between 0.1 g and 3 g and the duration of this first phase is between 1 millisecond and 100 milliseconds. The constant speed of the second phase depends on the speed of the assembly at the end of the first phase, and the duration of this second phase is between 0 and 5 seconds, and the acceleration of the third phase is of an intensity of between 0.1 g and 3 g, and the duration of this third phase is between 1 millisecond and 100 milliseconds.

Such characteristics make it possible to stimulate a living being, and in particular a human, without his or her vestibular system being saturated, which is generally the case beyond accelerations having an intensity of more than 3 g. Moreover, the duration of the accelerations is selected in such a way that the stimulation is considered as quasi-punctual, which makes it possible to discern clearly the response of the vestibular system to such stimulation.

According to yet another characteristic of the invention, the processing means are also capable of validating a cycle as a function of admissibility criteria regarding the movement of the eyes, and the shape and/or amplitude of the waves detected by the electrodes.

Thus, the processing means are capable of allowing an nth cycle after validation of the (n−1)th cycle, as well as restarting an nth cycle until it is validated.

In this way, each cycle retained can be considered as an exploitable cycle.

Advantageously, after validation of each cycle, the processing means are capable of delivering to a video monitor at least one image of the type consisting of a table of curves of evoked potentials representing the amplitude of the emission of the regions of the brain which is detected by each electrode in response to each stimulation phase of the cycle.

Preferably, the image delivered after an nth cycle, of a succession of identical cycles, represents the mean of the amplitudes detected during the course of the n identical cycles elapsed.

Thus, when the cycles of an examination are all identical, the image which is displayed on the screen as the cycles take place constitutes a consolidation of the whole of the images associated with the preceding cycles.

It then becomes possible for the person who is controlling the device (generally a specialist) to interrupt at any time the examination being carried out, when he judges that the response to the successive stimulations no longer progresses noticeably.

However, since the cycles of an examination can be different, repeated or not, successive or not, in the case of cycles which are different from one another, the image corresponding to the nth cycle represents the sole cycle number n.

According to yet another characteristic of the invention, the processing means also comprise a mass memory capable of storing in a register all the data resulting from each cycle of an examination, which data form examination results.

This makes it possible to analyse the results of an examination later, cycle by cycle, or even phase by phase.

To this end, the processing means are also capable of processing the data contained in at least one examination register, in order to transform them into potential field or current density data, and to deliver to the video monitor at least one image, of the "3D" three-dimensional type, of the surface of a cranial sphere of a living being, representing the data resulting from at least one nth cycle of the examination.

Advantageously, the mass memory is additionally capable of storing data relating to test examinations forming a data base, in order to permit at least one comparison, on the video monitor, between the results of at least one examination or of at least one nth cycle of at least one examination, and the data of at least one test examination.

It is thenceforward possible to make comparisons between subjects affected by pathology and normal subjects, or even between a plurality of subjects affected by different or identical pathologies.

In the preferred embodiment of the invention, the assembly additionally comprises a head support capable of preventing any movement of the head during an examination, a white noise generator capable of controlling parasitic auditory information, and also a visual mask capable of temporarily controlling visual information, which makes it possible to be more certain of the vestibular origin of the stimulation. Moreover, the device comprises at least two electrodes capable of detecting the horizontal and vertical movements of the eyes, and the processing means also comprise an amplification module for the signals detected by the electrodes.

Thus, the stimulated living being is isolated from the outside world, and especially from the auditory and visual stimulation capable of interfering with the vestibular information.

Other characteristics and advantages of the invention will be revealed by examining the detailed description below, and the accompanying drawings, in which: edited to here

The accompanying drawings are essentially certain in character. Consequently, they form an integral part of the description and can serve not only to complete the latter, but also to contribute to the definition of the invention if required.

Figure 1:
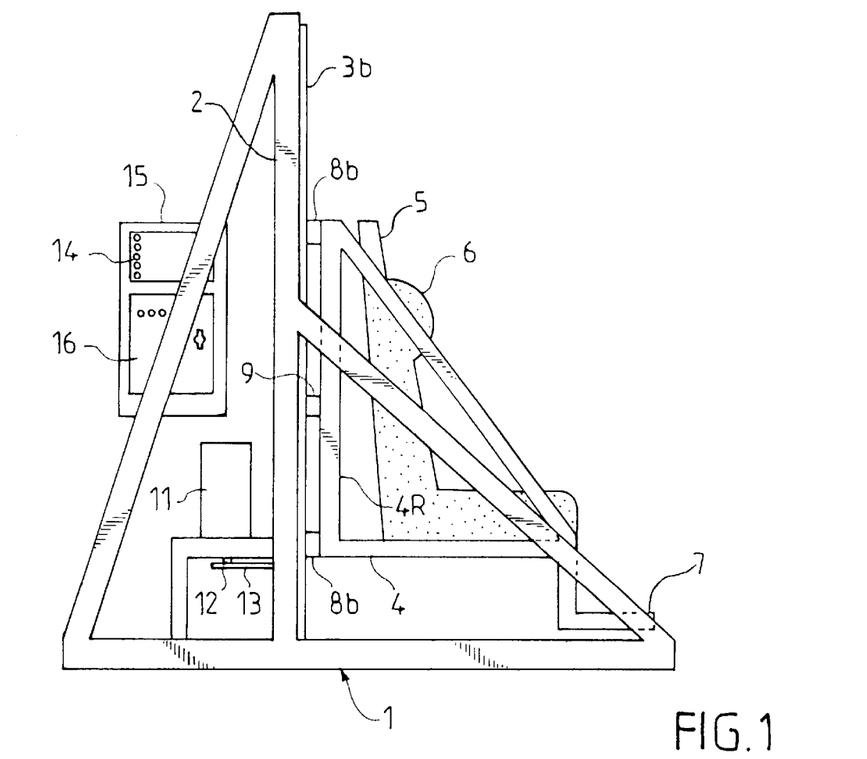
FIG. 1 is a diagrammatic side view of the frame and the movable assembly in an embodiment of the invention.
Figure 2:
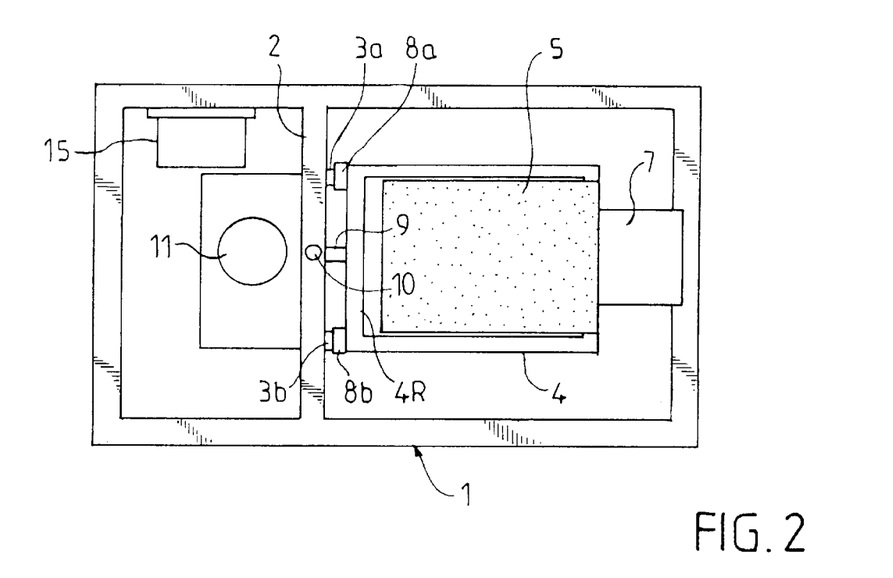
FIG. 2 is a top view of the frame and the movable assembly in an embodiment of the invention.

Reference is made firstly to FIGS. 1 and 2.

The object of the device is to stimulate the vestibular system of a living being, in particular a human, in an automated manner, and to process and analyse the data resulting from that stimulation.

To this end, the device consists of two distinct parts connected to each other: a mechanical part for stimulating the subject, and a second part capable, firstly, of controlling the first part, secondly, of detecting signals on the scalp of the subject, and thirdly, of processing the signals thus received.

The first part, which is essentially mechanical, comprises a frame 1, produced by assembling panels and rigid, solid components, permitting abrupt displacements of a movable assembly 4 able to support masses of approximately 200 kg within its structure.

In the embodiment described, the frame 1 comprises a vertical panel 2 on which are fixed two elements 3, also vertical, forming guide rails for a movable assembly 4.

The movable assembly 4 houses a chair 5, of the tub type, equipped with a harness (not shown in the figure), capable of keeping the body of the subject immobile for the duration of an examination.

The chair 5 also comprises a head support 6 suitable for immobilising the head of the subject in order to avoid any lateral movement.

The movable assembly 4 additionally comprises a footrest 7 adjustable in height.

Thus, a subject installed in the ergonomic chair 5, with the feet resting on the footrest 7, is not subjected to parasitic somesthesic afferences.

Moreover, the structure forming the movable assembly 4 comprises at the rear a metal frame 4R, substantially rectangular in shape, and equipped at each corner with a slider 8a or 8b capable of sliding inside one of the guide rails 3.

Thus, the two sliders 8a can slide in the guide rail 3a and, at the same time, the two sliders 8b can slide inside the rail 3b, taking the movable assembly 4 with them.

Finally, the metal frame of the movable assembly comprises fixing means 9 capable of causing the said assembly to slide on a vertical threaded rod 10 which forms an endless worm and is housed in a vertical pipe centred within the vertical panel 2 of the frame 1.

The endless worm 10 is driven in rotation by drive means comprising a stepping motor 11 provided with an output shaft 12. The shaft 12 is provided at its end with a pinion (not shown in the figures) capable of driving a synchronous belt 13 which also surrounds a second pinion (not shown in the figures) integral with the endless worm 10.

Thus, when the shaft 12 of the motor 11 is rotating, it drives the belt 13, which transmits the motion to the pinion integral with the endless worm 10, thus allowing the movable assembly 4 to be moved up or down in the frame 1.

The motor 11 is fed by a power unit 14 housed in a cabinet 15 fixed to the structure of the frame 1. The cabinet 15 also comprises an interface 16 for connection to mechanical control means which will be described later.

The second part of the device comprises a computer capable of controlling the motor 11, and also of processing and analysing data issuing from an electrophysiological helmet 17 which can be fitted onto the scalp of a subject installed in the chair 5.

Figure 3:
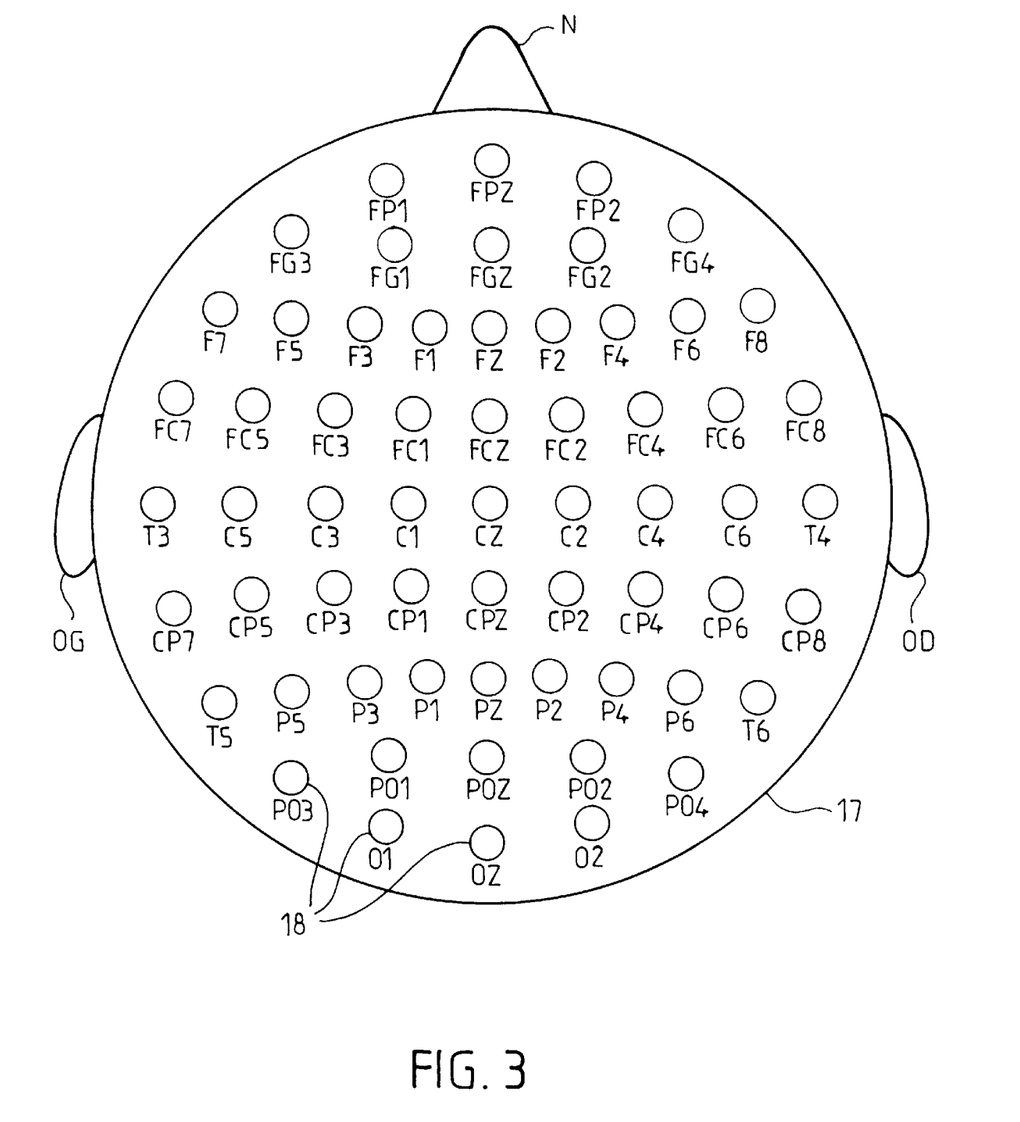
FIG. 3 is a view from below of the electrophysiological helmet, illustrating the position of the electrodes with reference to a skull.

Reference is now made to FIG. 3, which describes the electrophysiological helmet 17.

The helmet 17 comprises a plurality of electrodes 18. Depending on the accuracy of the examination, the helmet may include either 10 electrodes, 32 electrodes, or even 64 electrodes. In these three cases (10, 32, 64 electrodes), the electrophysiological helmet 17 meets the international standard 10/20.

By way of comparison, the helmet used by KAST and LANKFORD had only four electrodes, used in the position termed "AEP", that is to say: one earthing electrode (forehead), one reference electrode (vertex), and two active electrodes (right and left mastoid).

The helmet is made of a flexible material, and its shape is substantially spherical, which makes it possible to fit it onto the skull of a human type subject.

Nevertheless, any other helmet or assembly equipped with electrodes capable of detecting brain activity waves on the scalp of a subject may be used.

FIG. 3 shows the respective positions of the 32 electrodes with reference to the right ear OD and left ear OG, and also to the nose N of a human type subject. Each electrode defines a cerebral zone on the scalp of the subject, each cerebral zone being associated with at least one identifiable region of the brain, assumed to be a vestibular projection.

The electrodes 18 are capable of detecting brain activity waves emitted by one or more regions of the brain, in response to stimulation of the vestibular system, which stimulation is generated by the vertical translation of the movable assembly 4 in the frame 1.

The brain activity waves detected by the electrodes 18 will be picked up by processing and analysing means 23, in order to obtain therefrom vestibular evoked potentials, and to seek such evoked potentials which match the law of motion selected for stimulating the vestibular system of the subject.

In order to determine with the maximum accuracy the regions of the brain involved in the vestibular response to the stimulation, an analysis may be carried out of the evoked potentials by linear combination of some electrodes 18 of the helmet 17.

Moreover, in order to monitor to the best possible extent the vestibular origin of the stimulation, two annexed devices (not shown in the figures) are attached to the chair 5. The first annexed device is a white noise generator which makes it possible to suppress parasitic auditory information. The second annexed device is a system making it possible to suppress the visual information temporarily.

Finally, the device also comprises at least two electrodes (not shown in the figures) intended to be fixed in the vicinity of the eyelids of the subject in order to detect the vertical and horizontal movements of the subject's eyes.

Figure 4:
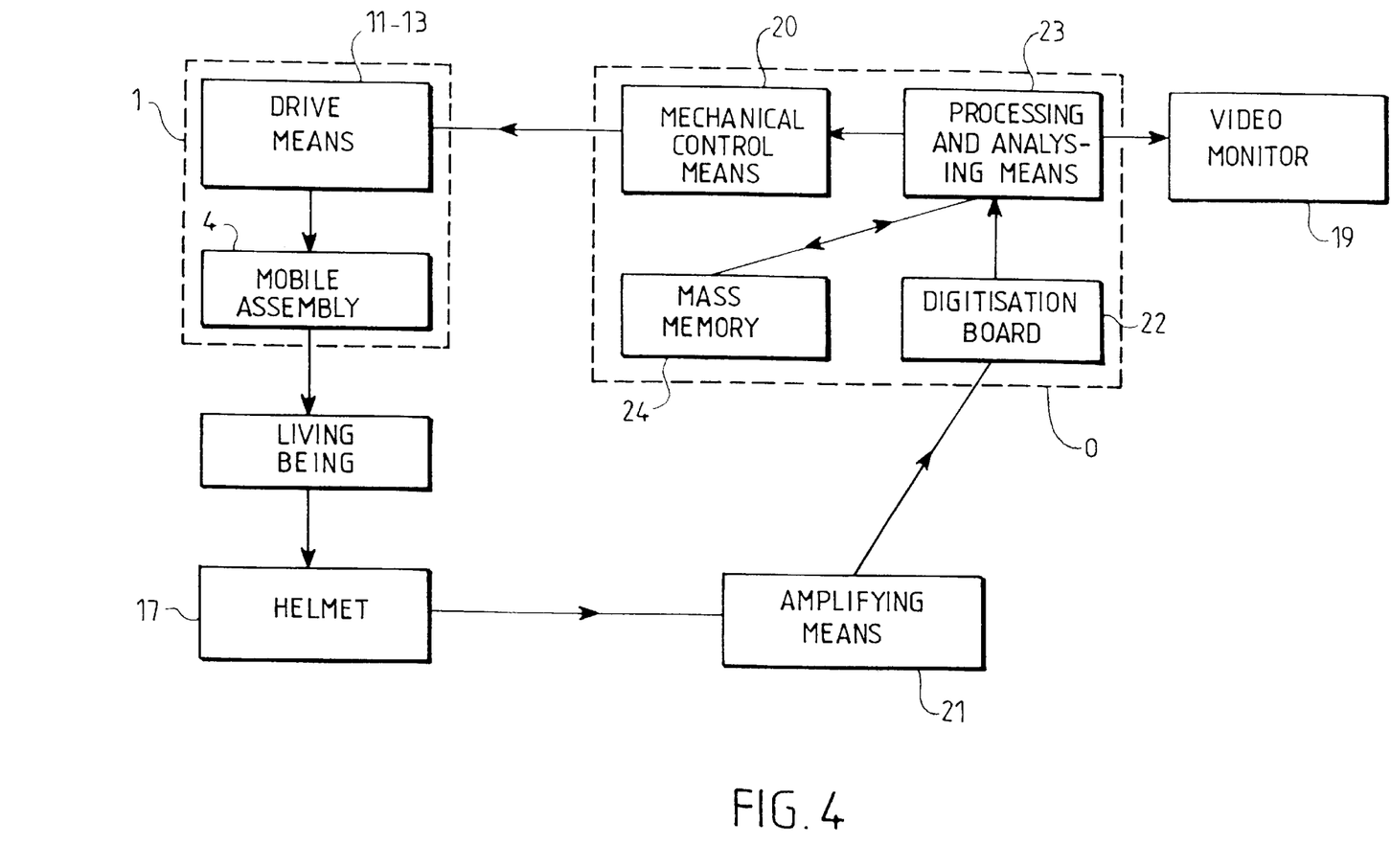
FIG. 4 shows the relationships between the principal elements of the device according to the invention.
Figure 5:
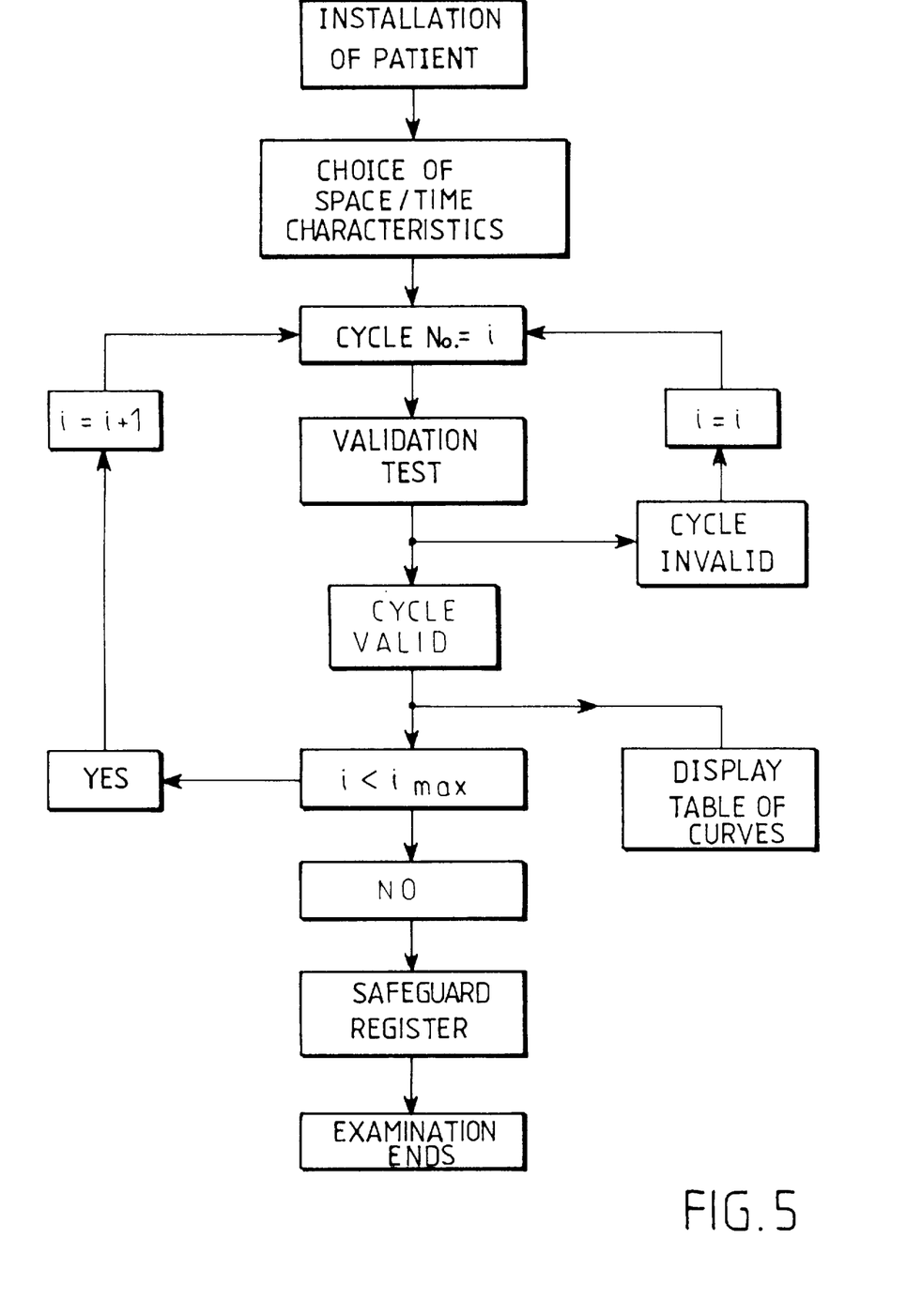
FIG. 5 is a flow chart illustrating the successive stages of a typical examination.

Reference is now made to FIGS. 4 and 5, in order to describe the connections between the different elements of the device and also the principal stages of an examination.

When a specialist decides to expose a subject to a vestibular examination, he first equips the subject with the helmet 17, the white noise generator, the system for suppressing visual information, and also at least two electrodes intended to detect ocular movements.

The subject is then installed in the chair 5 of the movable assembly 4. He or she is then immobilised in the chair 5 by means of the adjustable harness, and also the head support 6. The height of the footrest 7 can then be adjusted according to the height of the subject. The examination can then begin.

The specialist is installed in front of the console of his computer O. On the video screen 19 of the computer O is displayed a menu which allows him to select the monotonic space/time characteristics of the examination which he wishes to carry out.

By monotonic characteristic displacement there is to be understood any displacement carried out in the same direction during a determinate period corresponding to an elementary stimulation. In other words, this corresponds to a speed and/or an acceleration, either positive or nil, or negative or nil (deceleration).

A vestibular examination consists of the repetition of at least one stimulation cycle. A stimulation cycle comprises at least one stimulation phase termed elementary, selected from three phases:

a first phase in which the assembly is subjected to acceleration in a given direction of displacement, in the present case vertical, a second phase in which the assembly is subjected to a constant translation speed in that same direction of vertical displacement, and a third phase in which the assembly is subjected to deceleration in the same direction of displacement as that of the first and second phases.

The profile of the stimulation is therefore of any form whatsoever, such as, for example, trapezoidal, triangular or sinusoidal.

Moreover, the direction of linear displacement of an examination can be selected to be upwards (positive acceleration), then downwards (negative acceleration), or only upwards or only downwards.

The specialist thus selects the space/time characteristics of each phase of each cycle of the examination.

In general, an examination consists of the repetition of n identical cycles of three phases.

The space/time characteristics are the direction of translation, the number of repetitions and of phases of each cycle, the duration of each of the phases of each of the said cycles, and the intensity of the acceleration of each first and/or third phase of a cycle.

The speed of the second phase is that of the assembly 4 at the end of the first acceleration phase. It therefore depends not only on the intensity of the acceleration, but also on its duration.

In the embodiment proposed, the motor 11 is capable of subjecting the movable assembly to vertical monotonic accelerations of an intensity of between 0.1 g and 3 g during periods of between 1 millisecond and 100 milliseconds. The motor 11 can also subject the movable assembly 4 to a constant speed for a period of between 0 and 5 seconds.

Moreover, the duration of the acceleration phases has been selected in such a way that, on the one hand, the stimulation is considered by the vestibular system as being quasi-punctual and, on the other hand, it is possible to isolate the vestibular responses to that stimulation.

Once all of the space/time characteristics have been determined by the specialist, the computer O is capable of controlling the motor 11. For this, it comprises mechanical control means 20 which are connected by a linking cable to the interface 16 housed in the cabinet 15 of the frame 1.

Thus, at the command of the mechanical control means 20, the motor 11 will bring about the displacement of the assembly 4 in accordance with the space/time characteristics determined by the specialist.

Thus stimulated, the vestibular system of the subject, and in particular of the subject's otolithic system, since the example selected concerns stimulation of the vertical acceleration type, responds by emitting at the level of certain regions of the brain, brain activity waves which will be transmitted at the level of the scalp, then picked up by the electrodes 18 of the helmet 17.

The helmet 17 is connected to amplifying means 21, which are connected to a digitisation board 22 housed in the computer O.

The data gathered by the electrodes 18 are potential differences, the amplitude of which depends on the one hand on the number of neurones involved in the response, and on the other hand on the depth at which the part of the brain which is emitting is located.

These data will be digitised by the digitisation board 22, then processed in real time by the processing and analysing means 23 of the computer O. The data resulting from this processing form examination results. They will then be displayed on the video screen 19 of the computer, within a window, in the form of a table of curves of vestibular evoked potentials and in particular otolithic vestibular evoked potentials, each curve representing the signal received by an electrode 18 of the helmet 17.

The data resulting from processing by the processing and analysing means 23 are also stored in the form of registers, preferably of text format, in a mass memory 24 of the computer O.

The detailed procedure of an examination is as follows.

After the installation of the subject in the movable assembly 4, and the selection of the space/time characteristics of the examination, the specialist gives the command to the computer to start the examination. Let us assume a classic examination, that is to say, a single cycle repeated n times, each cycle consisting of three phases, a first acceleration phase, a second constant speed phase, and a third deceleration phase.

At the command of the control means 20 from the computer O, the motor 11 starts up, and imparts an acceleration to the movable assembly 4, thus bringing about its translation in an upward direction. The intensity of the acceleration of this first phase will be, for example 0.3 g, and the duration of this first phase is approximately 30 milliseconds.

Stimulated by such an acceleration, the vestibular system, and in particular the otolithic sub-system of the subject, responds by emitting, at the level of certain regions of the brain, brain activity waves. These waves are detected by the electrodes 18 of the electrophysiological helmet 17.

Each electrode 18 interprets the wave or waves thus detected at the level of the scalp as a potential difference of given amplitude. These 32 potential differences detected are then amplified by the amplifying means 21 which have 32 input paths and 32 output paths, then routed at the level of the digitisation board 22. Once digitised, the 32 signals are processed by the processing and analysing means 23, which subject all the potentials thus processed to admissibility criteria. These criteria constitute validity tests for the phase of the cycle being performed.

The two criteria are, firstly, the non-parasitising of the measurements by a visual afference detected by the analysis of the movements of the eyes, which is carried out by the two electrodes described previously, and, secondly, by a peak-clipping test of the potential at the level of the electrodes. The rejection criteria are effected in real time. Thus, the cycle which has elapsed is either validated or invalidated.

In the event of non-validation of the first cycle, the processing and analysing means 23 are capable of commanding the motor 11 to restart the whole of the cycle previously carried out. It is of course understood that this first cycle will be restarted as many times as the processing and analysing means 23 deem necessary.

In contrast, in the event of validation of the first cycle, the processing and analysing means 23 are capable firstly of displaying on the video monitor 19 a table of 32 evoked potential curves representing the waves detected by the 32 electrodes of the helmet 17, and secondly of commanding the motor 11 to carry out cycle number 2.

Figure 6:
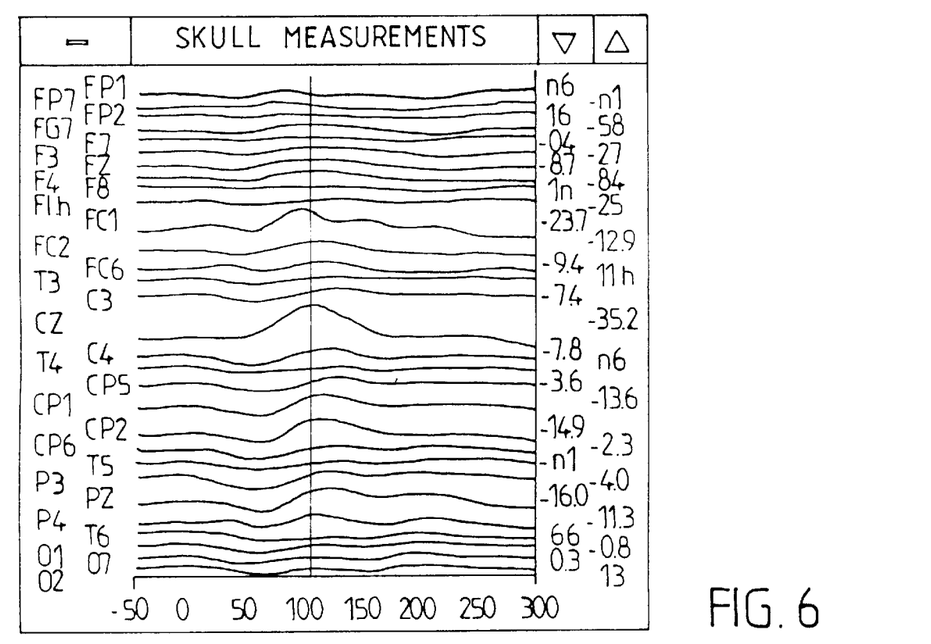
FIG. 6 is a screen copy illustrating a table of curves of otolithic evoked potentials, within a display window.

A table of this type is illustrated in FIG. 6, in which the axis of the abscissae represents the time in milliseconds, and the axis of the ordinates represents the amplitude of the evoked potential with respect to the zero of each curve. The left-hand axis of the ordinates is additionally used to designate different electrodes, and the right-hand axis of the ordinates is also used to indicate the maximum amplitude of each evoked potential.

This procedure is repeated until the nth cycle. At the end of this last cycle, all the data are stored in the form of an examination register in the mass memory 24 of the computer O.

In an examination register of this type, the data are stored cycle by cycle.

At the end of an examination, two possibilities are available to the specialist. A first possibility consists in carrying out another examination, identical to or different from the preceding one. In the first case, he selects the space/time characteristics of the examination to be carried out. The second possibility consists in analysing, immediately after the examination, all the data stored in the examination register. In this case, the specialist commands the computer O to display on the video screen 19 the table of curves of evoked potentials and/or a "3D" three-dimensional image representing a skull on which is shown, by means of a rectangle, the position of the electrodes with, in false colours round the said electrodes, zones representing the amplitude of the evoked potentials detected by each of the electrodes.

Figure 7:
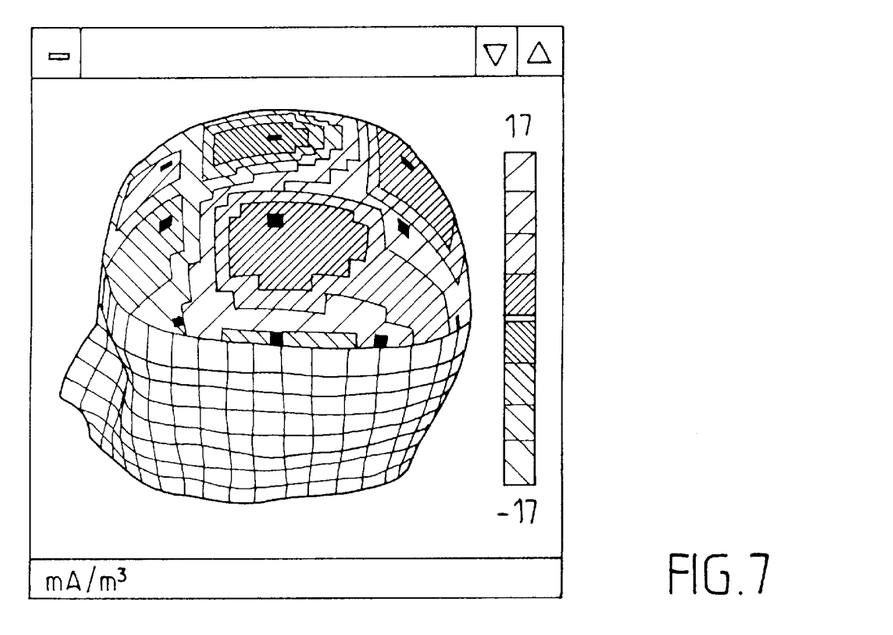
FIG. 7 is a screen copy illustrating a skull with, in false colours, potential fields arising from the processing of the results of an examination, with reference to a "3D" three-dimensional representation of a human skull equipped with electrodes.

A "3D" image of this type is illustrated in FIG. 7.

The processing and analysing means 23 are capable of supplying an image of the skull at any angle, and representing either potential fields or current density fields.

The potential fields or current density fields are calculated by the processing and analysing means 23 from the evoked potentials detected by the electrodes, using a mathematical calculation method termed "spherical spline".

This spherical spline method was initially developed by J. PERNIER, and disclosed in the article: "F. PERRIN, J. PERNIER, O. BERTRAND, and J. F. ECHALLIER, "Spherical splines for scalp potential and current density mapping", Electroencephalography and Clinical neurophysiology, 1989, 72, 184–187".

In fact, the calculation method used is an adaptation of the spherical spline method, which applies only to substantially spherical surfaces, which is not generally the case with the human scalp. This method has therefore been developed in order to take into account the non-sphericity of the brain case of a human. Consequently, it is called the quasi-spherical spline method.

Moreover, since the whole device is managed by a Windows environment (reg. trademark), the specialist can give the command for the display of a plurality of windows on the video screen 19, each window containing either a table of curves of evoked potentials, or a three-dimensional image of a skull representing potential fields or current density fields.

The processing and analysing means 23 are also capable of displaying within a window of the video screen 19 an evolving three-dimensional image, representing the evolution either of the potential fields or of the current density fields during the course of the different cycles of the examination in question. Thus, the specialist sees the evolution, over time and in a given window, of the activity of the different cerebral zones defined round each electrode.

It is also possible to display in several different windows the "3D" image of the same skull seen at different angles, or at different moments in time, or even representing either potential fields or current density fields. This latter solution makes it easier to analyse, in certain cases, the pathology of the subject examined, since the potential fields and the current density fields supply generally complementary information.

But it is also possible to display on the video screen 19, within different windows, examination results originating from different examinations carried out either on the same subject or on different subjects. Finally, the mass memory 23 of the computer O also contains test examination registers which form a data base, and which represent either known pathologies or normal subjects. Such a data base thus makes it possible to compare on the video screen 19 the results of an examination carried out on a subject with the data of a test examination which is well known.

In a particularly advantageous manner, the specialist can adjust the number of electrodes which will be processed by the processing and analysing means 23, then displayed on a table of curves of evoked potentials, or on a three-dimensional image of a skull. This makes it possible to make punctual analyses of privileged zones independently of the other zones.

It is also possible to vary the intensity of the colours in order to adjust the contrast of a three-dimensional image on the video screen 19.

In the description which has just been given, reference was made to a computer O for controlling the whole device. In fact, a micro-computer, or more generally any suitable means, firstly to control the displacement of the device, and secondly to process in real time the information acquired at the level of the scalp of the subject, then to store them in memory in order to allow them to be analysed later and compared with other information, can be used in place of a computer.

The invention as described would not be limited to this embodiment. A device could be produced which was equipped with a plurality of motors, each capable of displacing the movable assembly either in translation in a direction perpendicular to the vertical direction, as for example from front to rear, or laterally, or in rotation in a plane parallel to the plane of the ground.

But it is also possible to envisage combining translation with rotation. In order to permit such displacements, a suitable frame would be necessary.

Moreover, the drive means are not limited to the embodiment described above. Any other drive method capable of transmitting motion to the movable assembly may be envisaged. Finally, such a test device may be adapted to the examination of any living being. This implies that other types of chairs and of electrophysiological helmet may be used without thereby departing from the scope of the invention.

We claim:

1. A device for examining a subject and determining his or her vestibular evoked potentials, comprising:

a frame housing an assembly which is movable in at least one direction within the frame and supporting and immobilizing a subject;

drive means for moving the assembly in more than one direction to stimulate the subject's vestibular system;

an electrophysiological helmet fitted onto a scalp of the subject and provided with a plurality of electrodes, in selected respective positions, each electrode detecting brain activity waves issuing from identifiable regions of the subject's brain;

means for mechanically controlling the drive means according to a selected law of motion; and processing means for picking up the waves detected by the electrodes to obtain evoked potentials therefrom and to seek such evoked potentials which match the selected law of motion, wherein the drive means are arranged to permit displacement of the assembly in translation in more than one of three directions defining space and/or displacement of the assembly in rotation in one of three planes defining said space, wherein the means for mechanically controlling the drive means are arranged to permit application to the subject of moving elementary stimulation having monotonic space/time characteristics, with a profile which is adjustable in space and/or acceleration, in more than one of the three directions defining space in translation and/or in more than one of the said three planes of space in rotation, and wherein the processing means are for digitizing the waves detected by at least two of the electrodes, and are arranged to seek therein evoked potentials which match a profile a profile of the elementary stimulation, making it possible to obtain information in real time regarding functioning of at least a part of the vestibular system.

2. The device according to claim 1, wherein each datum of evoked potential is an amplitude which can be transformed on command by the processing means into a potential field or a current density field.

3. The device according to claim 1, wherein the processing means are for storing space/time examination characteristics in memory, each examination being defined by repetition of at least one stimulation cycle of at least one elementary stimulation phase selected from a first phase in which the assembly is subjected to acceleration in a given direction or a given direction of displacement, a second phase in which the assembly is subjected to a constant translation or rotation speed in that same direction or that same direction of displacement, and a third phase in which the assembly is subjected to deceleration in the same direction or the same direction of displacement as that of the first and second phases.

4. The device according to claim 3, wherein the space/time characteristics of an examination are the direction of translation and/or the direction of rotation of each cycle, a number of repetitions and of phases of each cycle, a duration of each of the phases of each of the cycles, and an intensity of the acceleration of each first and/or third phase of a cycle.

5. The device according to claim 3, wherein the acceleration of the first phase is of an intensity of between 0.1 g and 3 g, and a duration of this first phase between 1 millisecond and 100 milliseconds, wherein the constant speed of the second phase depends on the speed of the assembly at the end of the first phase, and a duration of the second phase is between 0 and 5 seconds, and wherein the acceleration of the third phase is of an intensity of between 0.1 g and 3 g, and a duration of this third phase is between 1 millisecond and 100 milliseconds.

6. The device according to claim 3, wherein the processing means are for validating a cycle as a function of admissibility criteria regarding movement of the eyes, and shape and/or amplitude of the waves detected by the electrodes.

7. The device according to claim 6, wherein the processing means are for allowing an nth cycle after validation of the (n−1)th cycle, as well as restarting an nth cycle until it is validated.

8. The device according to claim 6, wherein after validation of each cycle, the processing means are for delivering to a video monitor at least one image including a table of curves of evoked potentials representing the amplitude of an emission of regions of the subject's brain which is detected by each electrode in response to each stimulation phase of the cycle.

9. The device according to claim 8, wherein the image delivered after an nth cycle, of a succession of identical cycles, represents a mean of the amplitudes of the n identical cycles elapsed.

10. The device according to claim 8, wherein the processing means further comprise a mass memory for storing in a register all the data resulting from each cycle of an examination, which data form examination results.

11. The device according to claim 10, wherein the mass memory is for storing data relating to test examinations forming a data base, permitting at least one comparison, on the video monitor, between results of at least one examination or of at least one nth cycle of at least one examination, and the data of at least one test examination.

12. The device according to claim 1, wherein the assembly further comprises a head support for controlling any movement of the head during an examination, a white noise generator for controlling parasitic auditory information, and a visual mask for temporarily controlling visual information, making it possible to be more certain of a vestibular origin of the stimulation, wherein said mask comprises at least two electrodes for detecting horizontal and vertical movements of eyes, and wherein the processing means further comprises amplifying means for the signals detected by the electrodes.

13. A device for examining a subject and determining his or her vestibular evoked potentials, comprising:

a frame housing an assembly which is movable in at least one direction within the frame and supporting and immobilizing a subject;

drive means for moving the assembly in more than one direction to stimulate the subject's vestibular system;

an electrophysiological helmet fitted onto a scalp of the subject and provided with a plurality of electrodes, in selected respective positions, each electrode detecting brain activity waves issuing from identifiable regions of the subject's brain;

means for mechanically controlling the drive means according to a selected law of motion; and processing means for picking up the waves detected by the electrodes to obtain evoked potentials therefrom and to seek such evoked potentials which match the selected law of motion, wherein the drive means are arranged to permit displacement of the assembly in translation in more than one of three directions defining space and/or displacement of the assembly in rotation in one of three planes defining said space, wherein the means for mechanically controlling the drive means are arranged to permit application to the subject of moving elementary stimulation having monotonic space/time characteristics, with a profile which is adjustable in space and/or acceleration, in more than one of the three directions defining space in translation and/or in more than one of the said three planes of space in rotation, and wherein the processing means are for digitizing the waves detected by at least two of the electrodes, and are arranged to seek therein evoked potentials which match a profile a profile of the elementary stimulation, making it possible to obtain information in real time regarding functioning of at least a part of the vestibular system, and wherein the processing means are for processing the data contained in at least one examination register, transforming them into potential field or current density data, and to deliver to the video monitor at least one three-dimensional image of the surface of a cranial sphere of a subject, representing the data resulting from at least one nth cycle of the examination.

\* \* \* \* \*